(12) United States Patent
Wang et al.

(10) Patent No.: US 11,547,312 B2
(45) Date of Patent: Jan. 10, 2023

(54) SMART WATCH AND METHOD FOR MEASURING PULSE INFORMATION

(71) Applicant: BOE TECHNOLOGY GROUP CO., LTD., Beijing (CN)

(72) Inventors: Tieshi Wang, Beijing (CN); Xueling Gao, Beijing (CN); Zhiqiang Xu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 908 days.

(21) Appl. No.: 16/415,282

(22) Filed: May 17, 2019

(65) Prior Publication Data

US 2020/0069200 A1 Mar. 5, 2020

(30) Foreign Application Priority Data

Aug. 28, 2018 (CN) .......................... 201821389435.X (51) Int. Cl.
| | |
|---|---|
| *H04W 12/33* | (2021.01) |
| *A61B 5/024* | (2006.01) |
| *G02B 6/42* | (2006.01) |
| *A61B 5/00* | (2006.01) |
| *G04B 47/06* | (2006.01) |
| *G04G 21/02* | (2010.01) |
| *G06F 1/16* | (2006.01) |

(52) U.S. Cl.
CPC ...... *A61B 5/02433* (2013.01); *A61B 5/02438* (2013.01); *A61B 5/681* (2013.01); *A61B 5/6802* (2013.01); *G02B 6/4203* (2013.01); *G04B 47/063* (2013.01); *G04G 21/025* (2013.01); *G06F 1/163* (2013.01)

(58) Field of Classification Search
CPC ............ A61B 5/02433; A61B 5/02438; A61B 5/6802; A61B 5/681; A61B 5/02416; G02B 6/4203; G04B 47/063; G04G 21/025; G04G 9/0064; G06F 1/163; H04W 12/33
See application file for complete search history.

(56) References Cited

U.S. PATENT DOCUMENTS

| | | | |
|---|---|---|---|
| 10,238,305 B2 * | 3/2019 | Hingorani | .......... A61B 5/02438 |
| 2013/0266420 A1 * | 10/2013 | Kidane | ................... F01D 25/00 |
| | | | 415/118 |
| 2017/0032168 A1 * | 2/2017 | Kim | ..................... H04L 63/0861 |
| 2018/0317785 A1 * | 11/2018 | MacDonald | ....... A61B 5/14542 |
| 2018/0364557 A1 * | 12/2018 | Park | ......................... G04G 21/00 |
| 2020/0343433 A1 * | 10/2020 | Boukai | ................ G04G 21/025 |
| 2022/0022758 A1 * | 1/2022 | Eggers | ................... A61B 8/488 |

\* cited by examiner

*Primary Examiner* — Andrew Wendell
(74) *Attorney, Agent, or Firm* — Xsensus LLP (57) ABSTRACT

A smart watch and a method for measuring a pulse information are provided in the present disclosure. The smart watch includes a dial, a watchband, a blood vessel information collecting apparatus, and a processing apparatus. The watchband is connected with the dial. The blood vessel information collecting apparatus is disposed in the watchband and is configured to collect a blood vessel information from an inner side of a wrist of a user. The processing apparatus is connected with the blood vessel information collecting apparatus and is configured to receive and process the blood vessel information to obtain the pulse information of the user.

18 Claims, 9 Drawing Sheets

SMART WATCH AND METHOD FOR MEASURING PULSE INFORMATION

CROSS-REFERENCE TO RELATED APPLICATIONS

The present application claims the benefit of and priority to Chinese Patent Application No. 201821389435.X, filed on Aug. 28, 2018, which is incorporated herein by reference in its entirety.

TECHNICAL FIELD

The present disclosure relates to a field of smart wearable technology and, particularly, relates to a smart watch and a method for measuring a pulse information.

BACKGROUND

With the increasing development of wireless technology, smart wearable devices are gradually being favored. The development of smart watches is relatively mature. One of the main functions of the smart watches is to measure a heart rate (pulse) and provide a real-time detection for human health.

Currently, the main structure of the smart watches in the related art includes a dial, a watchband, and a measuring apparatus for measuring the pulse. The measuring apparatus is disposed on the back surface of the dial, that is, on the surface of the dial in contact with a skin of a wrist, and the heart rate of a user is measured through blood vessels in the back of the wrist.

The actual use indicates that an accuracy of measuring the heart rate by the smart watches in the related art is relatively low.

SUMMARY

According to one aspect of the present disclosure, a smart watch is provided in an embodiment of the present disclosure, including a dial, a watchband, a blood vessel information collecting apparatus, and a processing apparatus. The watchband is connected with the dial. The blood vessel information collecting apparatus is disposed in the watchband and is configured to collect blood vessel information from the inner side of a wrist of a user. The processing apparatus is connected with the blood vessel information collecting apparatus and is configured to receive and process the blood vessel information to obtain pulse information of the user.

According to an embodiment of the present disclosure, the blood vessel information collecting apparatus includes a transmitting optical fiber, a receiving optical fiber, and a fixing apparatus. The transmitting optical fiber is disposed in the watchband and is configured to have an input end and an output end. The receiving optical fiber is disposed in the watchband and is configured to have a receiving end and a transmitting end. The fixing apparatus is configured to fix the output end of the transmitting optical fiber and the receiving end of the receiving optical fiber. In the embodiment, the input end is connected with the processing apparatus, the output end is connected with the fixing apparatus, the receiving end is connected with the fixing apparatus, and the transmitting end is connected with the processing apparatus.

According to an embodiment of the present disclosure, the fixing apparatus includes a fixing plate and a fixing ring. The fixing plate is disposed on a surface of the watchband facing the wrist skin and is provided with a plurality of through holes. In the embodiment, the output ends of the transmitting optical fibers and the receiving ends of the receiving optical fibers are configured to extend through the through holes respectively and fixed by the fixing ring.

According to an embodiment of the present disclosure, the fixing apparatus further includes a diffusing apparatus and a fixing block. The diffusing apparatus, that is disposed on a surface of the fixing plate facing the skin and configured to correspond to a position of the transmitting optical fiber, is configured to increase an exit angle of an infrared light output from the transmitting optical fiber. The fixing block is configured to connect the diffusing apparatus to the fixing plate.

According to an embodiment of the present disclosure, the diffusing apparatus includes an antistatic layer, a polyethylene terephthalate layer, and a diffusion layer which are sequentially stacked.

According to an embodiment of the present disclosure, the fixing apparatus further includes a spotlight apparatus and a fixing block. The spotlight apparatus, that is disposed on a surface of the fixing plate facing the skin and configured to correspond to a position of the receiving optical fiber, is configured to increase an angle of a reflected light received by the receiving optical fiber. The fixing block is configured to connect the spotlight apparatus to the fixing plate.

According to an embodiment of the present disclosure, the fixing apparatus further includes a diffusing apparatus, a spotlight apparatus, and a fixing block. The diffusing apparatus, that is disposed on a surface of the fixing plate facing the skin and corresponding to a position of the transmitting optical fiber, is configured to increase an exit angle of an infrared light output from the transmitting optical fiber. The spotlight apparatus, that is disposed on a surface of the fixing plate facing the skin and corresponding to a position of the receiving optical fiber, is configured to increase an angle of an reflected light received by the receiving optical fiber. The fixing block is configured to connect the diffusing apparatus and the spotlight apparatus to the fixing plate respectively.

According to an embodiment of the present disclosure, the fixing apparatus includes a fixing plate and a fixing band. The fixing plate is disposed inside the watchband. The fixing band is configured to fix the output end of the transmitting optical fiber and the receiving end of the receiving optical fiber on the fixing plate.

According to an embodiment of the present disclosure, the output end of the transmitting optical fiber is oppositely disposed with the receiving end of the receiving optical fiber.

According to an embodiment of the present disclosure, both an end face of the output end of the transmitting optical fiber and an end face of the receiving end of the receiving optical fiber are perpendicular to a plane of the fixing plate.

According to an embodiment of the present disclosure, the fixing apparatus further includes a reflector plate disposed between the output end of the transmitting optical fiber and the receiving end of the receiving optical fiber.

According to an embodiment of the present disclosure, in the output end of the transmitting optical fiber and the receiving end of the receiving optical fiber, an optical fiber wall on the side away from the skin is longer than the optical fiber wall on the side adjacent to the skin.

According to an embodiment of the present disclosure, the processing apparatus includes an optical transmitter, an optical receiver, and a processor. The optical transmitter connecting with the transmitting optical fiber is configured to generate an infrared light. The optical receiver connecting with the receiving optical fiber is configured to receive a reflected light generated after the infrared light illuminating a skin and convert the reflected light into an electrical signal. The processor is connected with the optical transmitter and the optical receiver respectively and is configured to control the optical transmitter to generate the infrared light and receive the electrical signal sent by the optical receiver. The processor is further configured to process the electrical signal to obtain the pulse information.

According to an embodiment of the present disclosure, the watchband includes a first watchband and a second watchband. The first watchband includes: a first band body; a first interface located at one end of the first band body and connected with one side of the dial; and a first lock catch located at the other end of the first band body. The second watchband includes: a second band body; a second interface located at one end of the second band body and connected with the other side of the dial; and a second lock catch located at the other end of the second band body and connected with the first lock catch.

According to another aspect of the present disclosure, a method for measuring pulse information is provided in the present disclosure, using a smart watch for measurement. The smart watch includes a dial, a watchband, a blood vessel information collecting apparatus and a processing apparatus. The blood vessel information collecting apparatus is disposed in the watchband and is configured to collect a blood vessel information from the inner side of a wrist of a user. The processing apparatus is connected with the blood vessel information collecting apparatus and is configured to receive and process the blood vessel information to obtain a pulse information of the user.

The method for measuring pulse information includes:

the blood vessel information collecting apparatus collecting the blood vessel information from the inner side of the wrist of the user and transmitting the blood vessel information to the processing apparatus; and the processing apparatus receiving and processing the blood vessel information to obtain the pulse information.

According to an embodiment of the present disclosure, the blood vessel information collecting apparatus includes a transmitting optical fiber, a receiving optical fiber, and a fixing apparatus. The transmitting optical fiber is disposed in the watchband and is configured to have an input end and an output end. The receiving optical fiber is disposed in the watchband and is configured to have a receiving end and a transmitting end. The fixing apparatus is configured to fix the output end of the transmitting optical fiber and the receiving end of the receiving optical fiber.

The method further includes:

the processing apparatus generating an infrared light;

the infrared light being sent to the transmitting optical fiber through the input end of the transmitting optical fiber and being transmitted in the transmitting optical fiber;

the infrared light being emitted from the output end of the transmitting optical fiber and irradiating onto a skin of the inner side of the wrist of the user to form a reflected light on the skin;

the reflected light being sent to the receiving optical fiber through the receiving end of the receiving optical fiber and being transmitted in the receiving optical fiber;

the reflected light being sent to the processing apparatus through the transmitting end of the receiving optical fiber;

the processing apparatus processing the reflected light to obtain the pulse information.

According to an embodiment of the present disclosure, the processing apparatus includes an optical transmitter, an optical receiver, and a processor. The method further includes:

the optical transmitter generating an infrared light and sending the infrared light to the transmitting optical fiber;

the optical receiver receiving a reflected light and converting the reflected light into an electrical signal, and transmitting the electrical signal to the processor;

the processor receiving and processing the electrical signal to obtain the pulse information.

Understandably, implementing any one of the products or methods of the present disclosure does not necessarily require all of the advantages described above to be achieved at the same time. Other characteristics and advantages of the present disclosure will be set forth in the following specification, and partly will be apparent from the specification or understood by implementing the present disclosure. The objectives and other advantages of the present disclosure can be achieved and obtained by the structure particularly pointed out in the specification, claims, and accompanying drawings.

BRIEF DESCRIPTION OF THE DRAWINGS

The accompanying drawings are used to provide a further understanding of the technical solutions of the present disclosure, and constitute a part of the specification. The accompanying drawings are used to explain the technical solutions of the present disclosure together with the present application, and do not constitute a limitation of the technical solutions of the present disclosure. The shapes and sizes of the various components in the accompanying drawings do not reflect true proportions, and are merely intended to illustrate the content of the present disclosure.

DETAILED DESCRIPTION

A detailed description of the embodiments of the present disclosure is further described below in conjunction with the accompanying drawings. The following is used to illustrate the present disclosure, but is not used to limit the scope of the present disclosure. It should be noted that, in case of no conflict, characteristics in the present application can be arbitrarily combined with each other.

Smart watches in the related art of the field have a low accuracy in measuring a heart rate. The reason is that blood vessels in the back of a wrist are buried deeply, and a blood volume of each blood vessel is quite different. Therefore, there is a large error in measuring the heart rate by detecting the blood vessels on the back of the wrist. In addition, a layout of a measuring apparatus is limited and a measurable area is small due to a limited area of a dial, thereby the error is large. Therefore, a smart watch in which a measuring apparatus is disposed in a watchband to detect the blood vessels in the inner side of the wrist is provided in the present disclosure.

Figure 1:
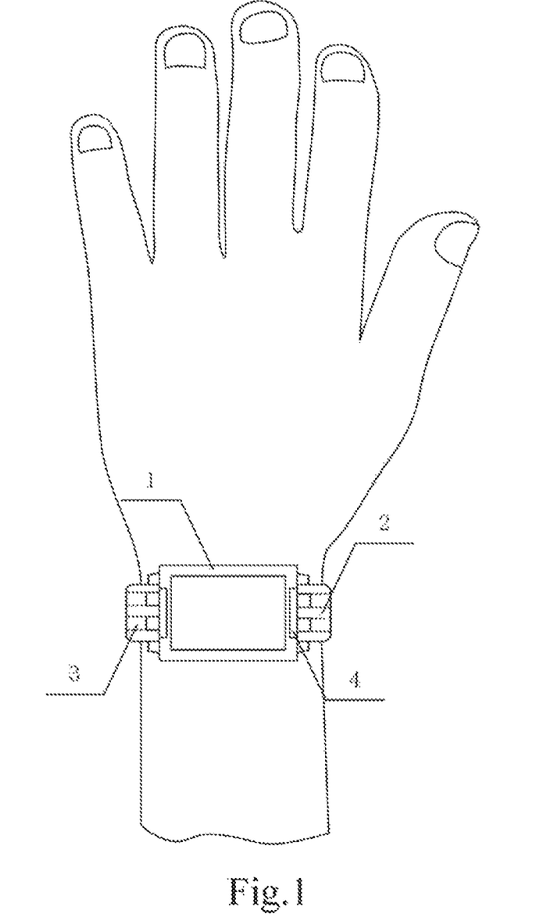
FIG. 1 is a structural schematic view of a using state of a smart watch of the present disclosure.
Figure 2:
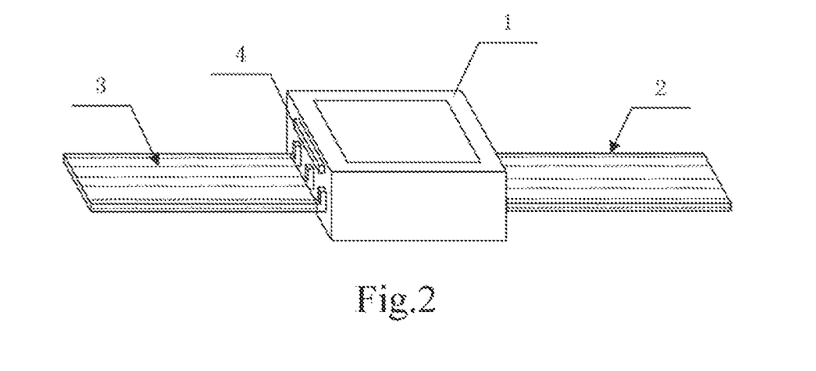
FIG. 2 is a structural schematic view of a unfolded state of a smart watch of the present disclosure.

FIG. 1 is a structural schematic view of a using state of the smart watch of the present disclosure. FIG. 2 is a structural schematic view of an unfolded state of the smart watch of the present disclosure. As shown in FIGS. 1 and 2, the main structure of the smart watch of the present disclosure includes a dial 1, a watchband 2, a blood vessel information collecting apparatus 3, and a processing apparatus 4. In an embodiment, the watchband 2 is disposed on both sides of the dial 1 and connected with the dial 1 for the user to wear the dial 1 on an outer side of the wrist. The blood vessel information collecting apparatus 3 is disposed in the watchband 2 for collecting a blood vessel information in the inner side of the wrist of the user and transmits the collected blood vessel information to the processing apparatus 4. The processing apparatus 4 is disposed on the dial 1 and connected with the blood vessel information collecting apparatus 3 for receiving the blood vessel information transmitted by the blood vessel information collecting apparatus 3, and obtains a pulse information (e.g., the heart rate information) of the user according to the blood vessel information.

In the present disclosure, the outer side of the wrist of the user refers to a wrist area on a side back of the hand, and the inner side of the wrist refers to the other wrist area that does not include the outer side of the wrist. The inner side of the wrist includes a wrist area on a side of the palm. The present disclosure collects the blood vessel information in the inner side of the wrist of the user by disposing the blood vessel information collecting apparatus in the watchband. Since the blood vessels in the inner side of the wrist are buried shallowly and a blood volume of each blood vessel is uniform, the smart watch of the present disclosure can collect a more accurate blood vessel information. The accuracy of measuring the pulse information is relatively high. In addition, since the blood vessel information collecting apparatus is disposed in the watchband, not only an area that can be disposed is large and convenient to lay out, but also the blood vessel information of multiple areas of the wrist can be collected. The accuracy of the pulse information measurement is further improved. Further, the present disclosure can directly obtain the pulse information of the user by disposing the processing apparatus on the dial without external device assistance. It is convenient and quick to use, suitable for all kinds of people, and has good application prospects.

The technical solutions of the present disclosure will be described in detail below through particular embodiments.

The First Embodiment

Figure 3:
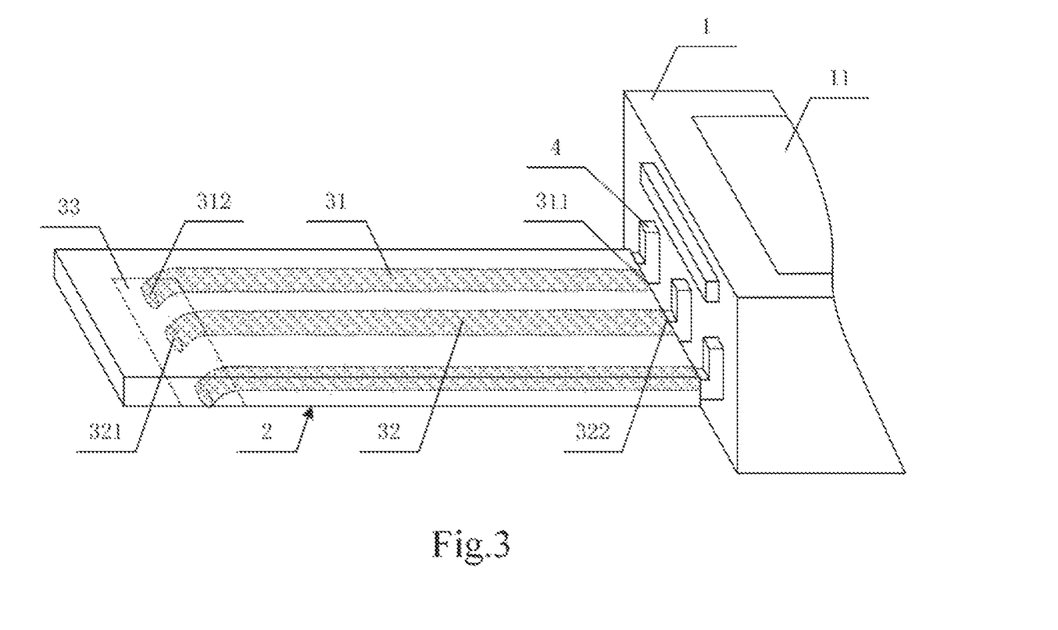
FIG. 3 is a structural schematic view of a transmitting optical fiber and a receiving optical fiber of the first embodiment of the present disclosure.
Figure 4:
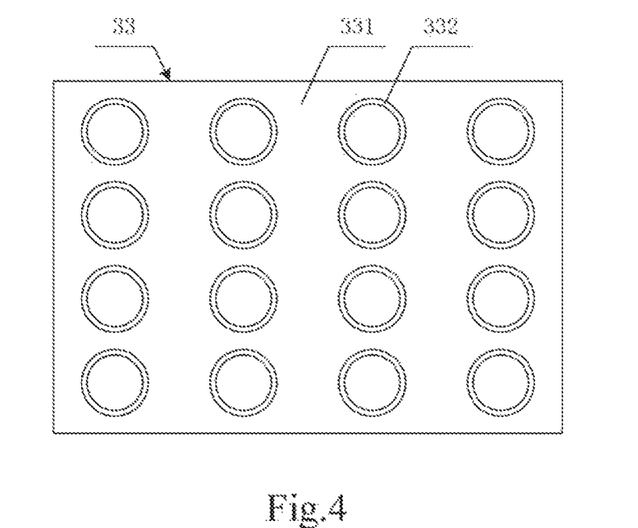
FIG. 4 is a structural schematic view of a fixing apparatus of the first embodiment of the present disclosure.
Figure 5:
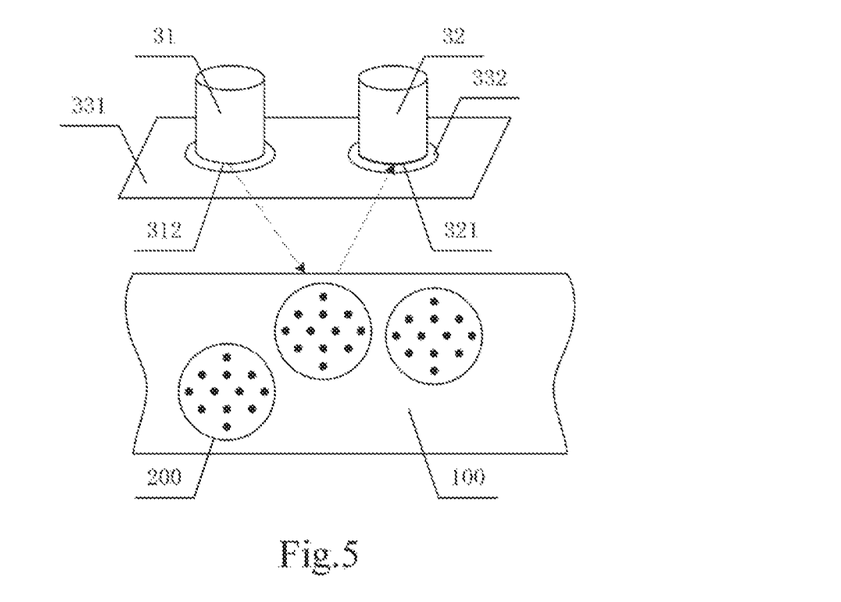
FIG. 5 is a structural schematic view of a blood vessel information collecting apparatus of the first embodiment of the present disclosure.

FIGS. 3 to 5 are structural schematic views of the first embodiment of the present disclosure. Among them, FIG. 3 is a structural schematic view of a transmitting optical fiber and a receiving optical fiber of the first embodiment of the present disclosure. FIG. 4 is a structure schematic view of a fixing apparatus of the first embodiment of the present disclosure. FIG. 5 is a structural schematic view of the blood vessel information collecting apparatus of the first embodiment of the present disclosure. As shown in FIG. 3, the main structure of the blood vessel information collecting apparatus of the present embodiment includes the transmitting optical fiber 31, the receiving optical fiber 32, and the fixing apparatus 33. A plurality of transmitting optical fibers 31 and receiving optical fibers 32 are all disposed inside the watchband 2 and extends along a length direction of the watchband 2. An input end 311 of each transmitting optical fiber 31 is connected with the processing apparatus 4. An output end 312 of each transmitting optical fiber 31 is connected with the fixing apparatus 33. A receiving end 321 of each receiving optical fiber 32 is connected with the fixing apparatus 33. A transmitting end 322 of each receiving optical fiber 32 is connected with the processing apparatus 4.

As shown in FIG. 4, the main structure of the fixing apparatus 33 of the present embodiment includes a fixing plate 331 and fixing rings 332. The fixing plate 331 is mounted on a surface of the watchband 2 facing the wrist skin, and a plurality of through holes are disposed thereon. Each of the through holes is provided with the fixing ring 332 for fixing an end of the optical fiber (the output end of the transmitting optical fiber and the receiving end of the receiving optical fiber). The output end 312 of the transmitting optical fiber 31 and the receiving end 321 of the receiving optical fiber 32 are configured to extend through the through holes respectively and fixed by the fixing ring 332. Both an end face of the output end 312 of the transmitting optical fiber 31 and an end face of the receiving end 321 of the receiving optical fiber 32 are parallel to a plane of the fixing plate 331, that is, parallel to a surface of the wrist skin of its position. In actual implementation, the fixing plate may be one or more fixing plates, which are disposed at a certain position or multiple different positions of the watchband according to actual needs to collect the blood vessel information in a particular area or multiple areas of the inner side of the wrist. The fixing plate may be adopted as having a shape, such as a rectangle, a circle, or an ellipse. The number and position of the through holes can be arranged according to actual needs or implementation requirements. The plurality of through holes are arranged in a form of a matrix when the plurality of through holes are disposed in the fixing plate. In order to facilitate the collection, each fixing plate is provided with an even number of through holes. Two adjacent through holes are formed a collection point. One of the two adjacent through holes is sleeved on the output end of the transmitting optical fiber, and the other through hole is sleeved on the receiving end of the receiving optical fiber.

As shown in FIG. 5, the transmitting optical fiber 31 and the receiving optical fiber 32 are respectively fixed on the fixing plate 331 through the fixing rings 332. The input end (not shown) of the transmitting optical fiber 31 is connected with the processing apparatus.

The transmitting end (not shown) of the receiving optical fiber 32 is connected with the processing apparatus. An infrared light generated by the processing apparatus enters the transmitting optical fiber 31 from the input end of the transmitting optical fiber 31 and transmitted via the transmitting optical fiber 31. The infrared light is emitted from the output end 312 of the transmitting optical fiber 31 and irradiated onto a skin 100 on the inner side of the wrist of the user. A reflected light returned from the skin 100 enters the receiving optical fiber 32 from the receiving end 321 of the receiving optical fiber 32 and is transmitted via the receiving optical fiber 32. The reflected light is output to the processing apparatus through the transmitting end of the receiving optical fiber 32. The processing apparatus processes the reflected light to obtain the pulse information of the user after receiving the reflected light.

Figure 6:
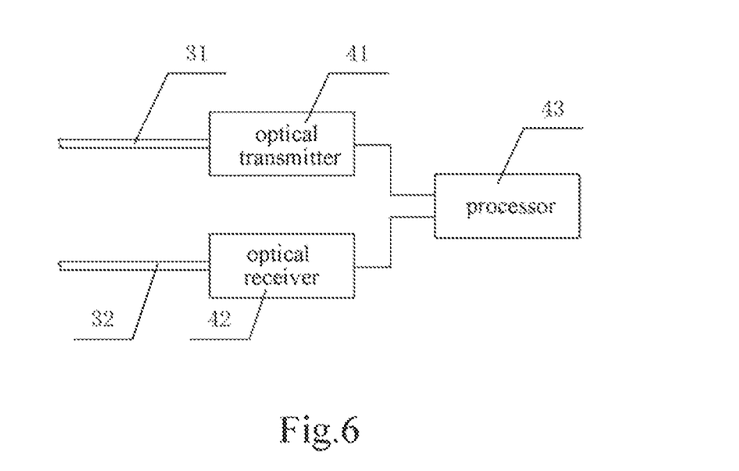
FIG. 6 is a structural schematic view of a processing apparatus of the first embodiment of the present disclosure.

FIG. 6 is a structural schematic view of the processing apparatus of the first embodiment of the present disclosure. As shown in FIG. 6, the main structure of the processing apparatus 4 includes an optical transmitter 41, an optical receiver 42, and a processor 43 connected with the optical transmitter 41 and the optical receiver 42, respectively. The optical transmitter 41 is connected with the transmitting optical fiber 31 and the optical receiver 42 is connected with the receiving optical fiber 32. In the embodiment, the optical transmitter 41 is configured to generate the infrared light under a control of the processor 43. The infrared light is transmitted via the transmitting optical fiber 31 and is illuminated onto the skin on the output end of the transmitting optical fiber. The optical receiver 42 is configured to receive the reflected light transmitted from the receiving optical fiber 32 under the control of the processor 43. The reflected light is first converted to an electrical signal and, then, the electrical signal is transmitted to the processor 43. The processor 43 processes the electrical signal to obtain the pulse information of the user.

As shown in FIGS. 3 to 6, a principle of obtaining the pulse information in the present embodiment is that, when a certain intensity of the infrared light generated by the optical transmitter 41 is irradiated onto the skin 100, blood cells in a subcutaneous venous blood vessel 200 will absorb some of the infrared light. Thus, in the reflected light returned from the skin 100, the reflected light of the position subcutaneously distributed with venous blood vessel 200 is significantly reduced. Also, a distribution of the subcutaneous venous blood vessel 200 can be known according to the received reflected light, and the processing apparatus can calculate the pulse (heart rate) information of the user through the blood vessel information collecting apparatus by collecting a distributed data of a series of subcutaneous venous blood vessel in different areas and at different times. A display screen 11 may be disposed on the dial 1. The processing apparatus 4 is connected with the display screen 11 to send the obtained pulse information of the user to the display screen 11 for presentation to the user. The principle, technical implementation, etc. for obtaining the heart rate information through a blood vessel measurement are technologies that all well known to those skilled in the art and will not be described herein.

In the present embodiment, positions of the optical transmitter, the optical receiver, and the processor can be flexibly disposed according to the dial structure. For example, the processor can be disposed either inside the dial or on a side of the dial, which only need to be connected with the optical transmitter and the optical receiver through signal lines. In another example, the optical transmitter and the optical receiver may be disposed on the same side of the dial or may be respectively disposed on both sides of the dial, as long as the dial is in a convenient location to be connected with the watchband, and the optical transmitter and the optical receiver are in a convenient location to be connected with the optical fiber. In actual use, the optical transmitter may adopt an optoelectronic means capable of generating the infrared light, such as a light emitting diode, a light emitting audion, or a combination of the light emitting diode and the light emitting audion. The optical receiver may adopt an optoelectronic means capable of converting the optical signal into the electrical signal, such as a photodiode, a phototransistor, or a combination of the photodiode and the phototransistor. The processor may adopt a digital signal processing (DSP) chip, which is not particularly limited in the present embodiment thereto.

In the present embodiment, the transmitting optical fiber emitting the infrared light to the skin of a disposed position and the receiving optical fiber receiving the reflected light from the skin of the disposed position are ensured through disposing the fixing apparatus that is configured to fix the input end of the transmitting optical fiber and the receiving end of the receiving optical fiber on the watchband, which ensures operational reliability. In the smart watch structure of the related technology in the art, since the measuring apparatus is disposed on the back of the dial, only a single collecting position is used and the collecting area is small, thereby there is a relatively large error. In contrast, the present embodiment can dispose a plurality of fixing apparatuses on the watchband to achieve the collection of the blood vessel information in multiple areas of the wrist. It is beneficial to eliminate the errors caused by the different burial depth of blood vessels in different areas and the uneven blood volume in each blood vessel. Meanwhile, since the blood vessels in the inner side of the wrist are buried shallowly and the blood volume of each blood vessel is uniform, a more accurate blood vessel information can be collected. In combination with the above technical means, the present disclosure maximizes to improve the accuracy of the pulse information measurement.

The Second Embodiment

Figure 7:
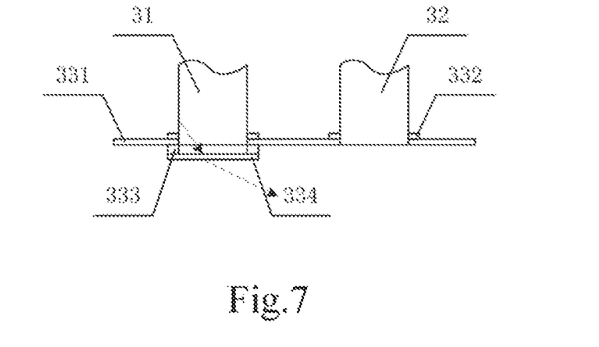
FIG. 7 is a structural schematic view of a fixing apparatus of the second embodiment of the present disclosure.

The present embodiment is an extension of the foregoing first embodiment. The main structure of the smart watch is the same as the foregoing first embodiment, and includes the dial, the watchband, the blood vessel information collecting apparatus, and the processing apparatus. The blood vessel information collecting apparatus includes the transmitting optical fiber, the receiving optical fiber, and the fixing apparatus. Different from the foregoing first embodiment, the fixing apparatus of the present embodiment further includes a diffusing apparatus. FIG. 7 is a structural schematic view of the fixing apparatus of the second embodiment of the present disclosure. As shown in FIG. 7, the fixing apparatus of the present embodiment includes the fixing plate 331, the fixing ring 332, a fixing block 333, and the diffusing apparatus 334. The structures of the fixing plate 331 and the fixing ring 332 are the same as that of the foregoing first embodiment. The diffusion apparatus 334 is disposed on a surface of the fixing plate 331 facing the skin and is connected with the fixing plate 331 through the fixing block 333. The diffusion apparatus 334 is disposed at a position corresponding to the transmitting optical fiber 31. The diffusing apparatus 334 of the present embodiment is configured to increase the exit angle of the infrared light output from the transmitting optical fiber 31. The range of the infrared light irradiating on the skin is expanded. The collection efficiency is improved by increasing the area of the irradiation area.

In one embodiment, the diffusion apparatus can be adopted a diffuser. Generally, the diffuser includes a material having a high light transmittance as a substrate. Scattering particles are added into the substrate to cause multiple refractions, reflections, and scattering when the light passing to achieve an effect of light diffusion. In another embodiment, the diffusing apparatus may be adopted a multilayer composite structure. For example, the diffusing apparatus includes an antistatic layer, a polyethylene terephthalate (PET) layer, and a diffusion layer which are sequentially stacked. In yet another embodiment, the diffusing apparatus may also be adopted a concave lens made of glass or plastic.

The present embodiment not only has the technical effects of the foregoing first embodiment, but also the irradiation area irradiated with the infrared light on the skin can be expanded and the collection efficiency is effectively improved through disposing the diffusing apparatus in the blood vessel information collecting apparatus. Further, static interference on the skin surface can be eliminated while achieving light diffusion through adopting the diffusion apparatus of a multilayer composite structure. The collection quality is improved.

The Third Embodiment

Figure 8:
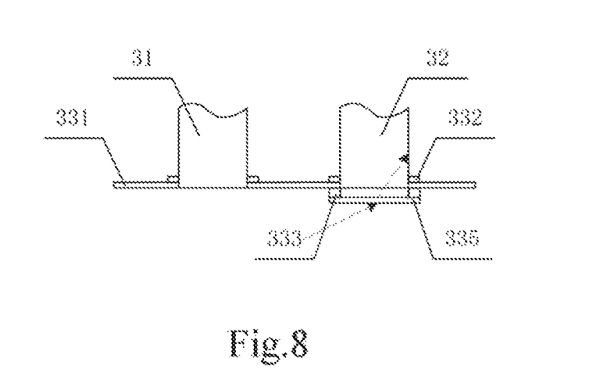
FIG. 8 is a structural schematic view of a fixing apparatus of the third embodiment of the present disclosure.

The present embodiment is an extension of the foregoing first embodiment. The main structure of the smart watch is the same as the foregoing first embodiment, and includes the dial, the watchband, the blood vessel information collecting apparatus, and the processing apparatus. The blood vessel information collecting apparatus includes the transmitting optical fiber, the receiving optical fiber, and the fixing apparatus. Different from the foregoing first embodiment, the fixing apparatus of the present embodiment further includes a spotlight apparatus. FIG. 8 is a structural schematic view of the fixing apparatus of the third embodiment of the present disclosure. As shown in FIG. 8, the fixing apparatus of the present embodiment includes the fixing plate 332, the fixing ring 332, the fixing block 333, and the spotlight apparatus 335. The structures of the fixing plate 332 and the fixing ring 332 are the same as that of the foregoing first embodiment. The spotlight apparatus 335 is disposed on a surface of the fixing plate 332 facing the skin and is connected with the fixing plate 331 through the fixing block 333. The spotlight apparatus 335 is disposed at a position corresponding to the receiving optical fiber 32. The spotlight apparatus 335 of the present embodiment is configured to increase an angle at which the receiving optical fiber 32 receives the reflected light. An increase in the angle at which the reflected light is received refers to an area of the collection area being expanded. The collection efficiency can be improved. In the present embodiment, the spotlight apparatus may also be adopted a convex lens made of glass or plastic.

The present embodiment not only has the technical effects of the foregoing first embodiment, but also the area of the collecting area can be expanded and the collection efficiency is effectively improved through disposing the spotlight apparatus in the blood vessel information collecting apparatus.

The Fourth Embodiment

Figure 9:
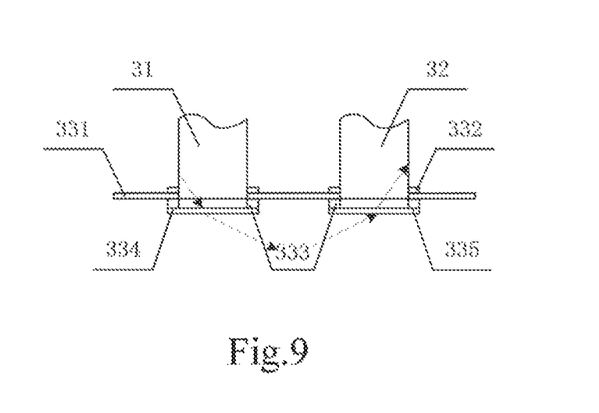
FIG. 9 is a structural schematic view of a fixing apparatus of the fourth embodiment of the present disclosure.

The present embodiment is a combination of the foregoing second embodiment and the third embodiment. The fixing apparatus of the present embodiment includes the diffusing apparatus and the spotlight apparatus. FIG. 9 is a structural schematic view of the fixing apparatus of the fourth embodiment of the present disclosure. As shown in FIG. 9, the fixing apparatus of the present embodiment includes the fixing plate 331, the fixing ring 331, the fixing block 333, the diffusing apparatus 334, and the spotlight apparatus 335. The diffusing apparatus 334 and the spotlight apparatus 335 are both disposed on a surface of the fixing plate 331 facing the skin. The diffusing apparatus 334 is disposed on a position corresponding to the transmitting optical fiber 31 and is connected with the fixing plate 331 through the fixing block 333. The spotlight apparatus 335 is disposed on a position corresponding to the receiving optical fiber 32 and is connected with the fixing plate 331 through the fixing block 333. In the embodiment, the diffusing apparatus 334 is configured to increase the exit angle of the infrared light output from the transmitting optical fiber 31 to expand the range of the infrared light irradiating on the skin. The spotlight apparatus 335 is configured to increase the angle at which the receiving optical fiber 32 receives the reflected light to expand the area of the collecting area. In the present embodiment, the diffusion apparatus and the spotlight apparatus may adopt the structures of the foregoing second embodiment and the third embodiment, respectively.

The present embodiment not only has the technical effects of the foregoing first embodiment, but also the irradiation area irradiated with the infrared light on the skin can be expanded by the diffusing apparatus, and the area of the collection area can be expanded by the spotlight apparatus through disposing the diffusing apparatus and the spotlight apparatus in the blood vessel information collecting apparatus. The collection efficiency is maximally improved.

The Fifth Embodiment

Although the foregoing first to fourth embodiments are described in a configuration in which the transmitting optical fiber and the receiving optical fiber are juxtaposed in the blood vessel information collecting apparatus; however, the blood vessel information collecting apparatus of the present disclosure may also be implemented by adopting another structural form. As long as the transmitting optical fiber can transmit the infrared light to the skin and the receiving optical fiber is capable of receiving the reflected light from the skin are ensured. The present disclosure is not particularly limited thereto. For example, in the blood vessel information collecting apparatus of the present embodiment, the transmitting optical fiber and the receiving optical fiber are configured to adopt a structure in which the transmitting optical fiber and the receiving optical fiber are disposed opposite to each other.

Figure 10A:
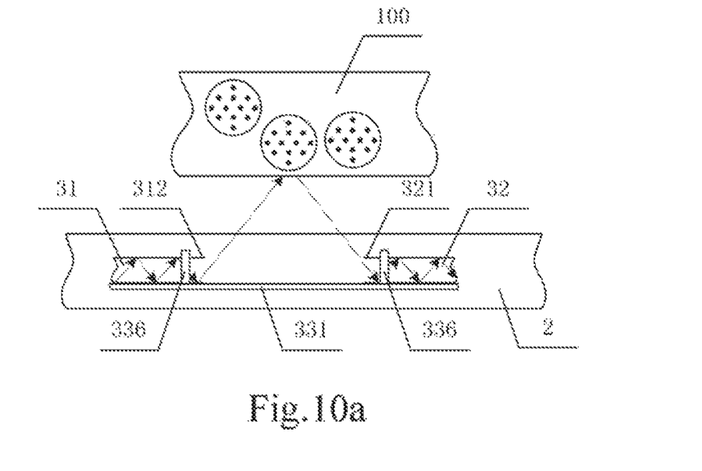
FIGS. 10a to 10c are structural schematic views of fixing apparatus of the fifth embodiment of the present disclosure.
Figure 10B:
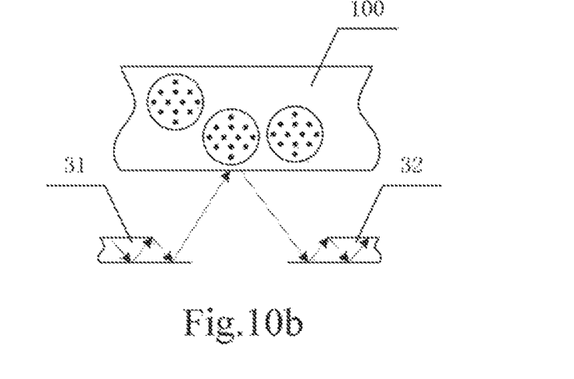
Figure 10C:
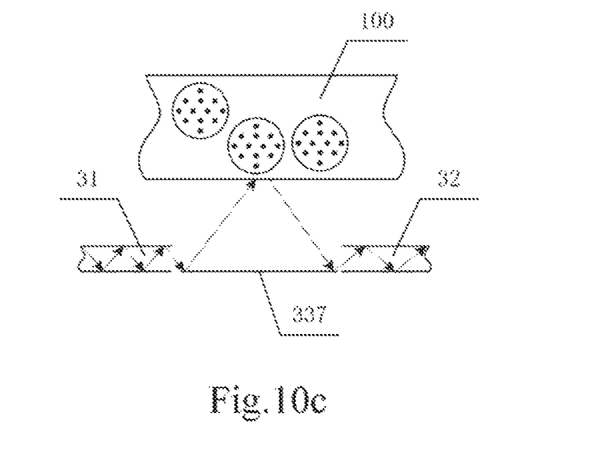

FIGS. 10a to 10c are structural schematic views of the fixing apparatus of the fifth embodiment of the present disclosure. As shown in FIG. 10a, the main structure of the smart watch of the present embodiment is the same as that of the foregoing embodiments, and includes the dial, the watchband, the blood vessel information collecting apparatus, and the processing apparatus. The blood vessel information collecting apparatus includes the transmitting optical fiber, the receiving optical fiber, and the fixing apparatus. A plurality of transmitting optical fibers and receiving optical fibers are all disposed inside the watchband and extend along the length direction of the watchband. The input end of each transmitting optical fiber is connected with the processing apparatus, and the output end is connected with the fixing apparatus. The receiving end of each receiving optical fiber is connected with the fixing apparatus, and the transmitting end is connected with the processing apparatus. Different from the foregoing embodiments, the main structure of the fixing apparatus includes the fixing plate 331 and a fixing band 336. The fixing plate 331 is disposed inside the watchband 2. The transmitting optical fiber 31 and the receiving optical fiber 32 are disposed on the fixing plate 331. The output end 312 of the transmitting optical fiber 31 and the receiving end 321 of the receiving optical fiber 32 are respectively fixed on the fixing plate 331 by the fixing band 336. Also, the output end 312 of the transmitting optical fiber 31 and the receiving end 321 of the receiving optical fiber 32 are oppositely disposed with a disposed distance therebetween. In the present embodiment, the end face of the output end 312 of the transmitting optical fiber 31 and the end face of the receiving end 321 of the receiving optical fiber 32 are both perpendicular to a plane of the fixing plate 331, that is, perpendicular to a surface of the wrist skin of its position. In actual implementation, the fixing plate may be one or more, which are disposed at a certain position or multiple different positions of the watchband according to actual needs to collect the blood vessel information of a specific area or multiple areas of the wrist. The fixing plate may adopt a shape, such as a rectangle, a circle, an ellipse, etc.

In the present embodiment, the infrared light generated by the processing apparatus enters the transmitting optical fiber 31 from the input end of the transmitting optical fiber 31 and is transmitted via the transmitting optical fiber 31. The infrared light is emitted from the output end 312 of the transmitting optical fiber 31 to irradiate to the skin 100 of the inner side of the user's wrist. The reflected light reflected from the skin 100 enters the receiving optical fiber 32 from the receiving end 321 of the receiving optical fiber 32 and is transmitted via the receiving optical fiber 32. The reflected light is transmitted to the processing apparatus through the transmitting end of the receiving optical fiber 32. The processing apparatus processes the reflected light to obtain the pulse information of the user after receiving the reflected light.

The present embodiment not only has the technical effects of the foregoing first embodiment, but also has a simple structure and facilitates the layout and fixation of the optical fiber. Meanwhile, the angle range of the light emitted from the output end of the transmitting optical fiber can be increased and the area of the irradiation area where the light is irradiated on the skin is expanded by utilizing the characteristics of the transmitting light in the optical fiber. The collection efficiency is effectively improved.

Based on the technical idea of the present embodiment, the structure of the present embodiment can also be optimized to further improve the collection efficiency. As shown in FIG. 10b, for example, the end face of the output end of the transmitting optical fiber and the end face of the receiving end of the receiving optical fiber may be disposed to be inclined. The optical fiber wall on the side away from the skin surface is longer than the optical fiber wall on the side adjacent to the skin surface. The protruding portion of the optical fiber wall is used as a reflecting surface. The range of angles at which the output end of the transmitting optical fiber emitting light and the receiving end of the receiving optical fiber receiving light are further increased to increase the luminous flux. As an implementation, the optical fiber wall on the side adjacent to the skin surface can be processed to a light transmission layer. As shown in FIG. 10c, for another example, a reflector plate 337 can be disposed on the fixing plate. The reflector plate 337 is disposed between the output end of the transmitting optical fiber and the receiving end of the receiving optical fiber. The angle range of the output end of the transmitting optical fiber emitting light and the angle range of the receiving end of the receiving optical fiber receiving light are further increased to increase the luminous flux through utilizing the reflector plate 337 as a reflection surface.

The Sixth Embodiment

Figure 11A:
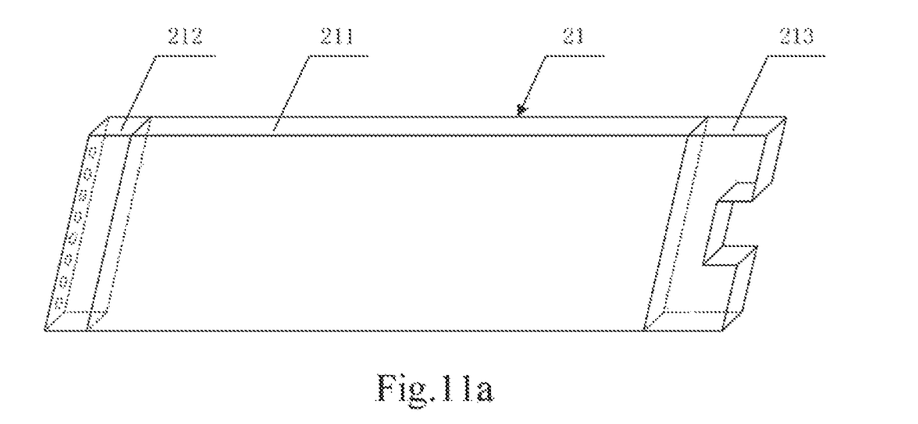
FIGS. 11a to 11c are structural schematic views of a watchband of the present disclosure.
Figure 11B:
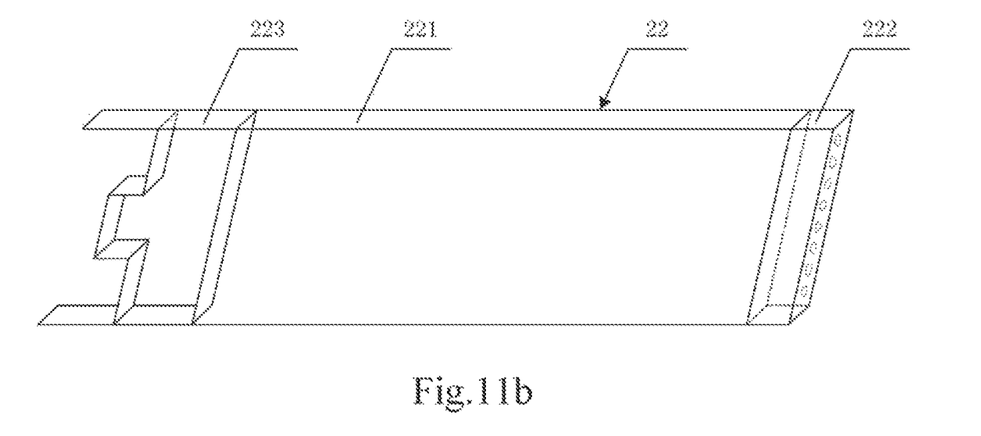

FIGS. 11a to 11c are structural schematic views of the watchband of the present disclosure. As shown in FIGS. 11a and 11b, the watchband includes a first watchband 21 and a second watchband 22. The main structure of the first watchband 21 includes a first band body 211, a first interface 212, and a first lock catch 213. The first interface 212 is located at one end of the first band body 211 of the first watchband 21 for connecting with one side of the dial. The first lock catch 213 is located at the other end of the first band body 211 of the first watchband 21 for connecting with the second watchband 22. The main structure of the second watchband 22 includes a second band body 221, a second interface 222, and a second lock catch 223. The second interface 222 is located at one end of the second band body 221 for connecting with the other side of the dial. The second lock catch 223 is located at the other end of the second band body 221 for connecting with the first watchband 21. The blood vessel information collecting apparatus of the foregoing embodiment is disposed in the first band body 211, disposed in the second band body 221, or disposed in the band body 211 and the second band body 221.

The present disclosure makes the watchband of the smart watch of the present disclosure can be replaced by providing the first interface 212 and the second interface 222 on the watchband to connect with the dial. Since the blood vessel information collecting apparatus is disposed in the watchband, even if different people use different dials or the same person replaces different dials at different periods, the heart rate monitoring is not affected. The compatibility is increased, and the field of employment is expanded.

Figure 11C:
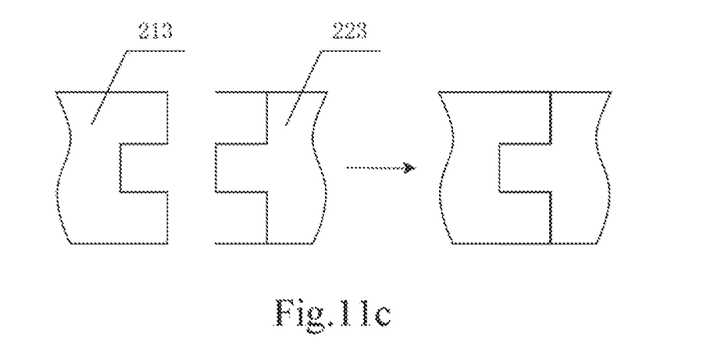

As shown in FIG. 11c, the first lock catch 213 and the second lock catch 223 of the present disclosure can adopt a magnet structure, and are connected by magnetic force after being worn. The magnet structures may be respectively disposed on a groove of the first lock catch 213 and a protrusion of the second lock catch 223. In addition, a guide plate may be disposed on the second lock catch 223. The lock catch structure of the present disclosure achieves a quick connection of the first watchband and the second watchband, has a simple structure, and is convenient to use.

The first band body 211 and the second band body 221 of the present disclosure may be made by adopting material such as nylon and flexible plastic etc. A plurality of mounting holes are defined inside of the first band body 211 and the second band body 221. The mounting holes extending along the length direction of the watchband and acting as an optical fiber channel to facilitate the mounting holes to wrap the optical fiber. All the structures of the first interface and the second interface as well as the structures of the first lock catch and the second lock catch etc. can be implemented by adopting the related mature technologies, and details are not described herein again.

A smart watch is provided in the present disclosure. The blood vessel information in the inner side of the wrist of the user is collected by disposing the blood vessel information collecting apparatus in the watchband. Since the blood vessels in the inner side of the wrist are buried shallowly and the blood volume of each blood vessel is uniform, the smart watch of the present disclosure can collect more accurate blood vessel information. The accuracy of the measured pulse information is relatively high. In addition, since the blood vessel information collecting apparatus is disposed in the watchband, not only is an area that can be disposed large and convenient to lay out, but also the blood vessel information of multiple areas of the wrist can be collected. The accuracy of the pulse information measurement is further improved. Further, the smart watch of the present disclosure can directly obtain the pulse information of the user by disposing the processing apparatus without external device assistance. It is convenient and quick to use, suitable for all kinds of people, and has good application prospects.

The Seventh Embodiment

Figure 12:
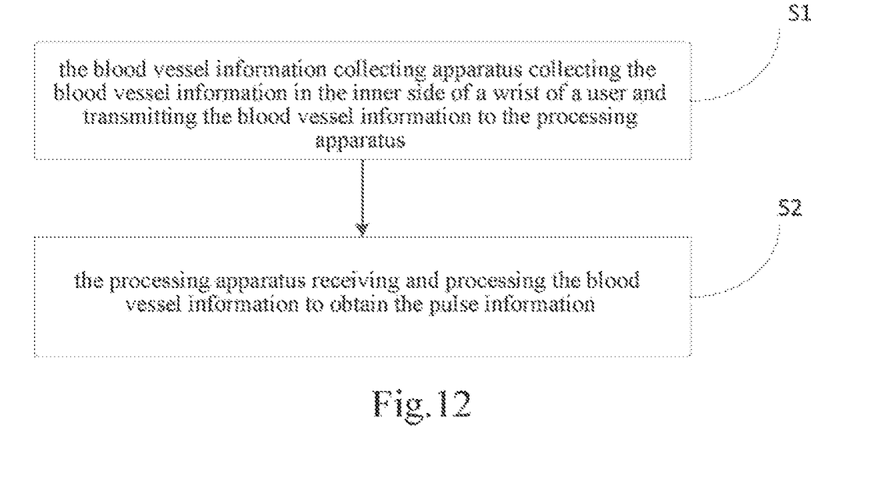
FIG. 12 is a flowchart of a method for measuring a pulse information of an embodiment of the present disclosure.

As shown in FIG. 12, a method for measuring the pulse information is provided in the present disclosure, which utilizes the smart watch in the above embodiments to measure pulse information. The above smart watch includes the dial 1, the watchband 2, the blood vessel information collecting apparatus 3, and the processing apparatus 4. The blood vessel information collecting apparatus 3 is disposed in the watchband 2 and configured to collect the blood vessel information in the inner side of the wrist of the user. The processing apparatus 4 is connected with the blood vessel information collecting apparatus 3 and configured to receive and process the blood vessel information to obtain the pulse information of the user. The method for measuring the pulse information includes the following steps:

S1. The blood vessel information collecting apparatus collects the blood vessel information in the inner side of the wrist of the user, and transmits the blood vessel information to the processing apparatus.

S2. The processing apparatus receives and processes the blood vessel information to obtain the pulse information.

The blood vessel information collecting apparatus 3 includes the transmitting optical fiber 31, the receiving optical fiber 32, and the fixing apparatus 33. The transmitting optical fiber 31 is disposed in the watchband 2 and has the input end 311 and the output end 312. The receiving optical fiber 32 is disposed in the watchband 2 and has the receiving end 321 and the transmitting end 322. The fixing apparatus 33 is configured to fix the output end 311 of the transmitting optical fiber 31 and the receiving end 321 of the receiving optical fiber 32. Other structures for the smart watch are the same as those of the smart watch in the above embodiments, and are not described herein again.

Figure 13:
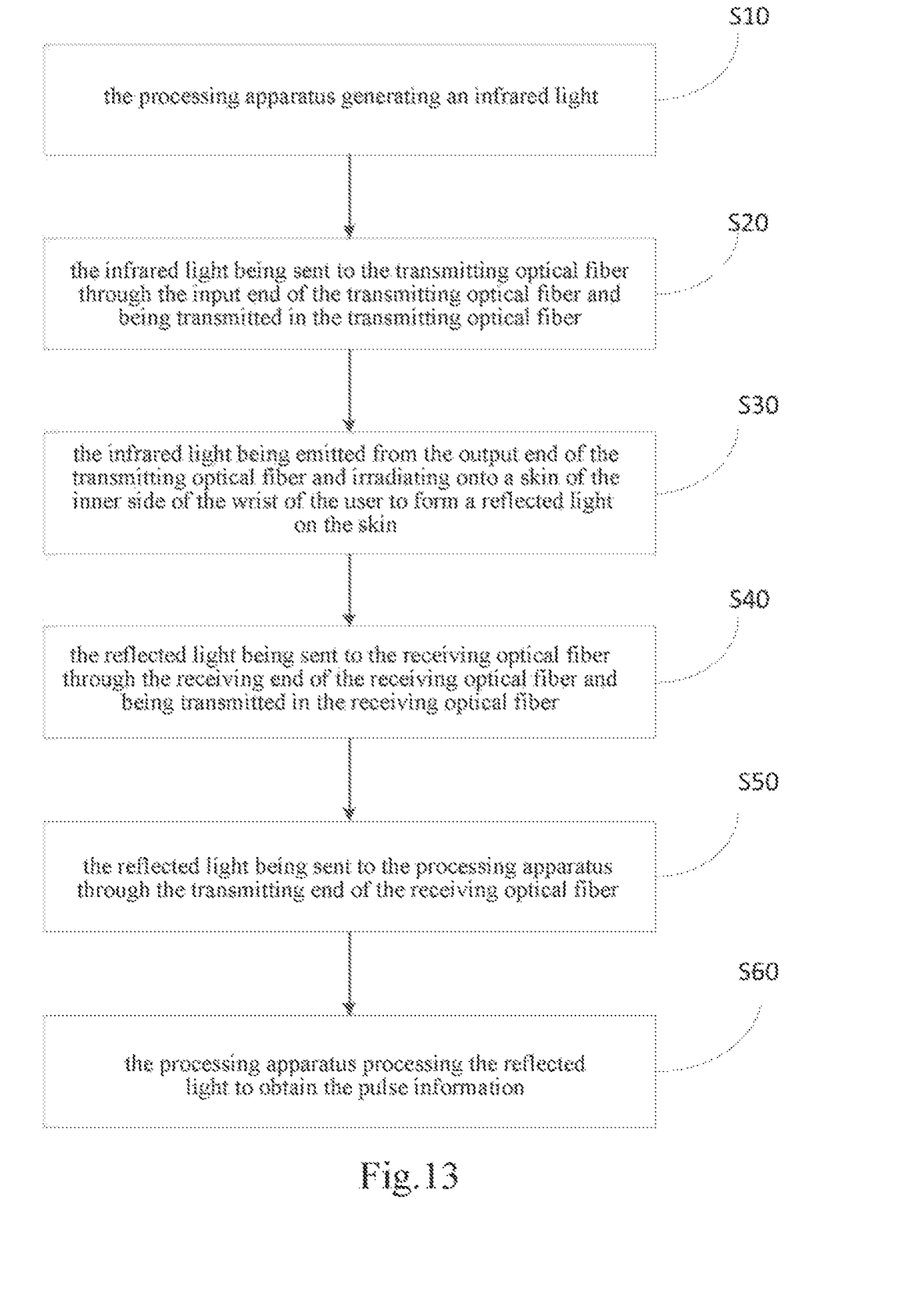
FIG. 13 is a flowchart of a method for measuring a pulse information of an embodiment of the present disclosure.

As shown in FIG. 13, the above method particularly includes the following steps:

S10. The processing apparatus generates the infrared light.

S20. The infrared light is sent to the transmitting optical fiber through the input end of the transmitting optical fiber and is transmitted in the transmitting optical fiber.

S30. The infrared light is emitted from the output end of the transmitting optical fiber and irradiated onto the skin of the inner side of the wrist of the user to form the reflected light on the skin.

S40. The reflected light is sent to the receiving optical fiber through the receiving end of the receiving optical fiber and transmitted in the receiving optical fiber.

S50. The reflected light is sent to the processing apparatus through the transmitting end of the receiving optical fiber.

S60. The processing apparatus processes the reflected light to obtain the pulse information.

Figure 14:
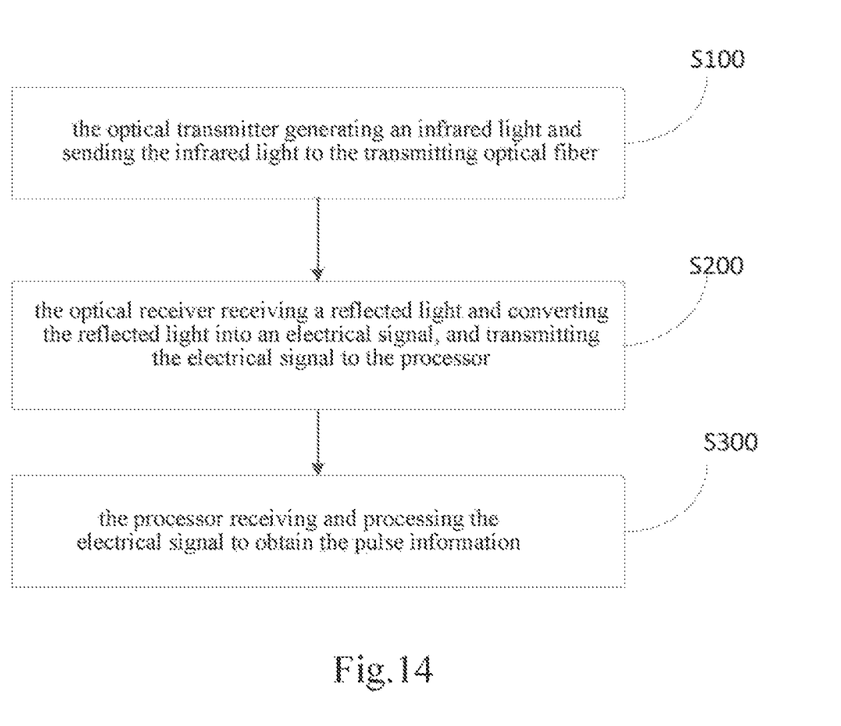
FIG. 14 is a flowchart of a method for measuring a pulse information of an embodiment of the present disclosure.

The processing apparatus in the above embodiment includes the optical transmitter 41, the optical receiver 42, and the processor 43. As shown in FIG. 14, the particular method steps for measuring by utilizing the processing apparatus 4 are as follows:

S100. The optical transmitter generates the infrared light and sends the infrared light to the transmitting optical fiber;

S200. The optical receiver receives the reflected light and converts the reflected light into an electrical signal, and transmits the electrical signal to the processor.

S300. The processor receives and processes the electrical signal to obtain the pulse information.

In the description of the present disclosure, it should be understood that, the orientation or position relationship indicated by the terms "middle", "upper", "lower", "front", "back", "vertical", "horizontal", "top", "bottom", "inside", "outside", etc., are based on the orientation or positional relationship shown in the accompanying drawings, which are only for convenience of describing the present disclosure and simplifying the description, and do not indicate or imply that the apparatus or component referred to must have a particular orientation and be constructed and operated in a particular orientation, therefore it should not be construed as limiting the disclosure.

In the description of the present disclosure, it should be noted that, unless otherwise expressly stated and limited, terms "mounted", "connected" and "connection" should be understood broadly. For example, it may be a fixed connection, a detachable connection, or an integral connection. It may be a mechanical connection, or may also be an electrical connection. It may be a direct connection, an indirect connection through an intermediate medium, or an internal connection between two components. The particular meanings of the above terms in the present disclosure can be understood in the particular circumstances by those skilled in the art.

Although the embodiments disclosed in the present disclosure are as described above, the described content is merely the embodiments adopted to facilitate the understanding of the present disclosure, and is not intended to limit the present disclosure. Any modification and variation in the form and details of the embodiments may be made by those skilled in the art without departing from the spirit and scope of the disclosure. However, the scope of patent protection of the present disclosure is still subject to the scope defined by the appended claims.

What is claimed is:

1. A smart watch, comprising:
   a dial;
   a watchband connected to the dial;
   a blood vessel information collecting apparatus disposed in the watchband, configured to collect blood vessel information in the inner side of a wrist of a user; and
   a processing apparatus connected to the blood vessel information collecting apparatus, the processing apparatus being configured to receive and process the blood vessel information to obtain pulse information of the user;
   wherein the blood vessel information collecting apparatus comprises:
   a transmitting optical fiber disposed in the watchband having an input end and an output end;
   a receiving optical fiber disposed in the watchband having a receiving end and a transmitting end;
   a fixing apparatus configured to fix the output end of the transmitting optical fiber and the receiving end of the receiving optical fiber; and
   wherein the input end is connected to the processing apparatus, the output end is connected to the fixing apparatus, the receiving end is connected to the fixing apparatus, and the transmitting end is connected to the processing apparatus.

2. The smart watch according to claim 1, wherein the fixing apparatus comprises:

a fixing plate disposed on a surface of the watchband facing the wrist skin, the fixing plate provided with a plurality of through holes;
a fixing ring; and
wherein the output end of the transmitting optical fiber and the receiving end of the receiving optical fiber are configured to extend through the plurality of through holes respectively and be fixed by the fixing ring.

3. The smart watch according to claim 2, wherein the fixing apparatus further comprises:
a diffusing apparatus disposed on a surface of the fixing plate facing the skin, the diffusing apparatus being configured to correspond to a position of the transmitting optical fiber, and being configured to increase an exit angle of an infrared light output from the transmitting optical fiber; and
a fixing block configured to connect the diffusing apparatus to the fixing plate.

4. The smart watch according to claim 2, wherein the diffusing apparatus comprises an antistatic layer, a polyethylene terephthalate layer, and a diffusion layer which are sequentially stacked.

5. The smart watch according to claim 2, wherein the fixing apparatus further comprises:
a spotlight apparatus disposed on a surface of the fixing plate facing the skin, the spotlight apparatus being configured to correspond to a position of the receiving optical fiber, and being configured to improve an angle of a reflected light received by the receiving optical fiber; and
a fixing block configured to connect the spotlight apparatus to the fixing plate.

6. The smart watch according to claim 2, wherein the fixing apparatus further comprises:
a diffusing apparatus disposed on a surface of the fixing plate facing the skin, the diffusing apparatus being configured to correspond to a position of the transmitting optical fiber, and being configured to increase an exit angle of an infrared light output from the transmitting optical fiber;
a spotlight apparatus disposed on the surface of the fixing plate facing the skin, the spotlight apparatus being configured to correspond to a position of the receiving optical fiber, and being configured to increase an angle of a reflected light received by the receiving optical fiber; and
a fixing block configured to connect the diffusing apparatus and the spotlight apparatus to the fixing plate; respectively.

7. The smart watch according to claim 2, wherein the fixing apparatus comprises:
a fixing plate disposed inside the watchband; and
a fixing band configured to fix the output end of the transmitting optical fiber and the receiving end of the receiving optical fiber on the fixing plate.

8. The smart watch according to claim 7, wherein the output end of the transmitting optical fiber is oppositely disposed with the receiving end of the receiving optical fiber.

9. The smart watch according to claim 8, wherein both an end face of the output end of the transmitting optical fiber and an end face of the receiving end of the receiving optical fiber are perpendicular to a plane of the fixing plate.

10. The smart watch according to claim 7, wherein the fixing apparatus further comprises a reflector plate disposed between the output end of the transmitting optical fiber and the receiving end of the receiving optical fiber.

11. The smart watch according to claim 7, wherein, in the output end of the transmitting optical fiber and the receiving end of the receiving optical fiber, an optical fiber wall on the side away from the skin is longer than an optical fiber wall on the side adjacent to the skin.

12. The smart watch according to claim 1, wherein the processing apparatus comprises:
an optical transmitter connected to the transmitting optical fiber, the optical transmitter being configured to generate an infrared light;
an optical receiver connected to the receiving optical fiber, the optical receiver being configured to receive a reflected light generated after the infrared light illuminates skin and convert the reflected light into an electrical signal; and
a processor connected to the optical transmitter and the optical receiver, respectively, the processor being configured to control the optical transmitter to generate the infrared light and receive the electrical signal sent by the optical receiver, and being configured to process the electrical signal to obtain the pulse information.

13. The smart watch according to claim 1, wherein the watchband comprises:
a first watchband, comprising:
a first band body;
a first interface located at a first end of the first band body, the first interface connected to a first side of the dial;
a first lock catch located at a second end of the first band body;
a second watchband, comprising:
a second band body;
a second interface located at a first end of the second band body, the second interface connected to a second side of the dial; and
a second lock catch located at a second end of the second band body, the second lock catch being connected to the first lock catch.

14. A method for measuring pulse information using a smart watch, comprising:
providing the smart watch, wherein the smart watch comprises:
a dial;
a watchband;
a blood vessel information collecting apparatus disposed in the watchband, the blood vessel information collecting apparatus being configured to collect blood vessel information in an inner side of a wrist of a user and comprising:
a transmitting optical fiber disposed in the watchband having an input end and an output end;
a receiving optical fiber disposed in the watchband having a receiving end and a transmitting end; and
a fixing apparatus configured to fix the output end of the transmitting optical fiber and the receiving end of the receiving optical fiber; and
a processing apparatus connected to the blood vessel information collecting apparatus, the processing apparatus being configured to receive and process the blood vessel information to obtain pulse information of the user;
generating, by the processing apparatus, an infrared light, wherein:
the infrared light is sent to the transmitting optical fiber through the input end of the transmitting optical fiber and transmitted in the transmitting optical fiber;

the infrared light is emitted from the output end of the transmitting optical fiber and irradiates onto skin of the inner side of the wrist of the user to form a reflected light on the skin;

the reflected light is sent to the receiving optical fiber through the receiving end of the receiving optical fiber and is transmitted in the receiving optical fiber; and the reflected light is sent to the processing apparatus through the transmitting end of the receiving optical fiber; and processing, by the processing apparatus, the reflected light to obtain the pulse information.

15. The method for measuring the pulse information according to claim 14, wherein:

the processing apparatus comprises an optical transmitter, an optical receiver, and a processor;

the method further comprises:

generating, by the optical transmitter, an infrared light and sending the infrared light to a transmitting optical fiber;

receiving, by the optical receiver, a reflected light, converting the reflected light into an electrical signal, and transmitting the electrical signal to the processor; and receiving and processing, by the processor, the electrical signal to obtain the pulse information.

16. The method for measuring the pulse information according to claim 14, wherein the fixing apparatus comprises:

a fixing plate disposed on a surface of the watchband facing skin of the wrist, the fixing plate being provided with a plurality of through holes;

a fixing ring; and wherein the output end of the transmitting optical fiber and the receiving end of the receiving optical fiber are configured to extend through the through holes, respectively, and be fixed by the fixing ring.

17. The method of measuring the pulse information according to claim 16, wherein the fixing apparatus further comprises:

a diffusing apparatus disposed on a surface of the fixing plate facing the skin, the diffusing apparatus being configured to correspond to a position of the transmitting optical fiber, and being configured to increase an exit angle of an infrared light output from the transmitting optical fiber; and a fixing block configured to connect the diffusing apparatus to the fixing plate.

18. The method of measuring the pulse information according to claim 16, wherein the fixing apparatus further comprises:

a spotlight apparatus disposed on a surface of the fixing plate facing the skin, the spotlight apparatus being configured to correspond to a position of the receiving optical fiber, and being configured to increase an angle of the reflected light received by the receiving optical fiber; and a fixing block configured to connect the spotlight apparatus to the fixing plate.

* * * * *